(12) United States Patent
Masuda et al.

(10) Patent No.: US 8,513,296 B2
(45) Date of Patent: Aug. 20, 2013

(54) PHARMACEUTICAL COMPOSITION

(75) Inventors: Takaaki Masuda, Yokohama (JP);
Naoko Kobayashi, Yokohama (JP);
Hideaki Sasagawa, Yokohama (JP)

(73) Assignees: Pola Pharma Inc., Shinagawa-ku, Tokyo (JP); Nihon Nohyaku Co., Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/603,220

(22) Filed: Sep. 4, 2012

(65) Prior Publication Data

US 2012/0329845 A1    Dec. 27, 2012

Related U.S. Application Data

(63) Continuation of application No. 12/676,346, filed as application No. PCT/JP2008/066056 on Sep. 5, 2008, now abandoned.

(30) Foreign Application Priority Data

Sep. 5, 2007    (JP) ................................. 2007-229619

(51) Int. Cl.
*A61K 31/4178*    (2006.01)
*A61P 31/10*    (2006.01)

(52) U.S. Cl.
USPC .......................................... 514/397; 424/61

(58) Field of Classification Search
None
See application file for complete search history.

(56) References Cited

U.S. PATENT DOCUMENTS

| | | | |
|---|---|---|---|
| 4,267,169 A | 5/1981 | Kamishita et al. |
| 4,636,520 A | 1/1987 | Umio et al. |
| 4,764,381 A | 8/1988 | Bodor et al. |
| 5,340,836 A | 8/1994 | Reinhard et al. |
| 5,690,923 A | 11/1997 | De Vringer et al. |
| 5,753,256 A | 5/1998 | Cordes et al. |
| 5,814,305 A | 9/1998 | Laugier et al. |
| 5,962,536 A | 10/1999 | Komer |
| 5,993,787 A | 11/1999 | Sun et al. |
| 6,007,791 A | 12/1999 | Coombes et al. |
| 6,008,256 A | 12/1999 | Haraguchi et al. |
| 6,017,920 A | 1/2000 | Kamishita et al. |
| 6,083,518 A | 7/2000 | Lindahl |
| 6,428,654 B1 | 8/2002 | Cronan, Jr. et al. |
| 6,585,963 B1 | 7/2003 | Quan et al. |
| 6,740,326 B1 | 5/2004 | Meyer et al. |
| 8,058,303 B2 | 11/2011 | Miki et al. |
| 2003/0017207 A1 | 1/2003 | Lin et al. |
| 2003/0235541 A1 | 12/2003 | Maibach et al. |
| 2004/0208906 A1 | 10/2004 | Tatara et al. |
| 2005/0232879 A1 | 10/2005 | Sasagawa et al. |
| 2006/0140984 A1 | 6/2006 | Tamarkin et al. |
| 2007/0099932 A1 | 5/2007 | Shirouzu et al. |
| 2008/0031835 A1 | 2/2008 | Kawamura et al. |
| 2009/0030059 A1 | 1/2009 | Miki et al. |
| 2009/0076109 A1 | 3/2009 | Miki et al. |
| 2009/0099202 A1 | 4/2009 | Shirouzu et al. |
| 2009/0137651 A1 | 5/2009 | Kobayashi et al. |
| 2009/0202602 A1 | 8/2009 | Ishima et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2010/0210703 A1 | 8/2010 | Vontz et al. |
| 2012/0014893 A1 | 1/2012 | Kobayashi et al. |
| 2012/0022120 A1 | 1/2012 | Kobayashi et al. |
| 2012/0149745 A1 | 6/2012 | Kobayashi et al. |

FOREIGN PATENT DOCUMENTS

| | | |
|---|---|---|
| EP | 0 070 525 | 1/1983 |
| EP | 0 440 298 | 8/1991 |
| EP | 0 715 856 | 6/1996 |
| EP | 1 138 314 | 10/2001 |
| EP | 1 522 316 | 4/2005 |
| EP | 1 537 868 | 6/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |
| JP | 61-118315 | 6/1986 |
| JP | 62-093227 | 4/1987 |

(Continued)

OTHER PUBLICATIONS

Vieira, et al. "Cationic Lipids and Surfactants as Antifungal Agents: Mode of Action," *Journal of Antimicrobial Chemotherapy*, Vo. 58, pp. 760-767, 2006.
SDS Density downloaded from www.chemicalbook.com/ChemicalProductProperty_EN_CB2147453.htm 2 pages.
Pluronics Density downloaded from www.chemicalbook.com/ChemicalProductPropertyEN_Cb2709101.htm, 2 pages, copyright 2010.
Ethyl Cellulose Density downloaded from www.chemicalbook.com/ProductMSDSDetailCB6165620_EN.htm, 3 pages, copyright 2008.
GHS Classification Guidance for Enterprises ($2^{nd}$ Edition, Ministry of Economy, Trade and Industry, Japan, Mar. 2010.

(Continued)

*Primary Examiner* — Dennis Heyer
(74) *Attorney, Agent, or Firm* — Knobbe, Martens, Olson & Bear LLP

(57) ABSTRACT

Disclosed is an antifungal agent for external use, which is characterized by containing a compound represented by the general formula (1) below, 50-95% by mass of an alcohol, and 0.1-35% by mass of water and/or an anionic surfactant.

General formula (1)

X = a halogen or H

18 Claims, No Drawings

(56) References Cited

FOREIGN PATENT DOCUMENTS

| | | |
|---|---|---|
| JP | 62-223163 | 10/1987 |
| JP | 1-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 07-74144 | 8/1995 |
| JP | 07-206711 | 8/1995 |
| JP | 07-223971 | 8/1995 |
| JP | 08-020527 | 1/1996 |
| JP | 10-152433 | 6/1998 |
| JP | 10-226639 | 8/1998 |
| JP | 10-226686 | 8/1998 |
| JP | 2001-064206 | 3/2001 |
| JP | 2002-114680 | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-104924 A | 4/2005 |
| JP | 2005-154306 | 6/2005 |
| JP | 2005-239678 | 9/2005 |
| JP | 2005-289879 | 10/2005 |
| JP | 2006-028123 | 2/2006 |
| JP | 2006-306734 | 11/2006 |
| RU | 2 270 894 C2 | 3/2004 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2006/038317 | 4/2005 |
| WO | WO 2005/099764 | 10/2005 |
| WO | WO 2005/123136 | 12/2005 |
| WO | WO 2007/102242 | 9/2007 |
| WO | WO 2007/077806 | 12/2007 |
| WO | WO 2008/075207 | 6/2008 |
| WO | WO 2010/093992 | 8/2010 |

OTHER PUBLICATIONS

Crotamiton Properties (http://www.chemspider.com/Chemical-Structure.2780.html) 2 pages.

Absolute ethanol MSDS (www.sciencelab.com/msds.php?msdsld=9923955) 7 pages.

Methyl Ethyl Ketone MSDS (www.sciencelab.com/msds.php?msdsld=9927358) 6 pages.

Niwano, et al. "Lanoconazole and Its Related Optically Active Compound NND-502: Novel Antifungal Imidazoles with a Ketene Dithioacetal Structure," *Current Medicinal Chemistry*, vol. 2, pp. 147-160, 2003.

Niwano, et al. "In vitro and in vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.

Martins, et al. "In vitro Sensitivity of Dermatophytes to Urea," *Clinics*, vol. 61, No. 1, pp. 9-14, 2006.

Uchida, et al. "In vitro Antifungal Activity of Luliconazole (NND-502), a Novel Imidazole Antifungal Agent," *Journal of Infectious Chemotherapy*, vol. 10, pp. 216-219, 2004.

Article, "Treatment" in 2 pages downloaded from http://www.babymd.net/dryskin.htm date unknown.

Supplemental European Search Report dated Aug. 10, 2010, issued to corresponding European patent application 06811053.5.

Supplementary European Search Report mailed Aug. 16, 2010 and issued to European application No. 06811056.8-2123/2005958.

Examination Report issued Apr. 8, 2010 to corresponding New Zealand Patent Application No. 571818.

International Search Report dated Nov. 18, 2008 issued to international application No. PCT/JP2008/066057.

Office action issued to related Israeli Patent Application No. 193894 on Oct. 14, 2010 with translation.

Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.

Niwano, et al. "Efficacy of NND-502, A Novel Imidazole Antimycotic Agent, in Experimental Models of *Candida albicans* and *Aspergillus fumigatus* Infections," *International Journal of Antimicrobial Agents*, vol. 12, pp. 221-228, 1999.

Uchida, et al. "In vitro Activity of Novel Imidazole Antifungal Agent NND-502 Against *Malassezia* Species," *International Journal of Antimicrobial Agents*, vol. 21, pp. 234-238, 2003.

Uchida, et al. "In vitro Antifungal Activity of Luliconazole (NND-502), a Novel Imidazole Antifungal Agent," *J Infect Chemother*, vol. 10, pp. 216-219, 2004.

Supplementary European Search Report issued Aug. 12, 2010 to corresponding European application No. 08829061.4.

International Search Report dated Nov. 18, 2008 and issued to priority international application No. PCT/JP2008/066056.

Pharmaceutical Interview Form, published in Apr. 2005; accessed from Homepage of Pharmaceuticals and Medical Devices Agency, http://www.info.pmda.go.jp/go/pack/2655712N1020_202/.

Office Action issued in corresponding European Patent Application No. 08829061.4, on Apr. 19, 2013.

Office Action issued in corresponding Japanese Patent Application No. 2009-531290, mailed on Apr. 23, 2013.

PHARMACEUTICAL COMPOSITION

CROSS-REFERENCE TO RELATED APPLICATIONS

This application is a continuation of U.S. application Ser. No. 12/676,346, filed Mar. 3, 2010 which is the U.S. National Phase under 35 U.S.C. §371 of International Application PCT/JP2008/066056, filed Sep. 5, 2008, which was published in a non-English language, which claims priority to JP Application No. 2007-229619, filed Sep. 5, 2007.

TECHNICAL FIELD

The present invention relates to a skin agent for external use, and more specifically, to an antifungal agent for external use.

BACKGROUND ART

For diseases such as athlete's foot and candidiasis to be caused by fungi, medicaments such as bifonazole, butenafine, and terbinafine have been developed and prescribed as skin medicines for external use.

Of those, there may be exemplified, as a particularly promising medicament, a compound represented by a general formula (1) having an effect of shortening a therapeutic period for diseases derived from fungi, which has been reported in recent years as a novel imidazole compound having an antifungal activity, especially, luliconazole, which is an optically active substance (see JP 3278738 B). Further, such compound is also useful for onychomycosis, and a formulation for onychomycosis has also already been known (for example, see WO 03/105841). That is, the compound represented by the general formula (1) may be said as a useful active ingredient that may be widely used for mycoses (having an antifungal action).

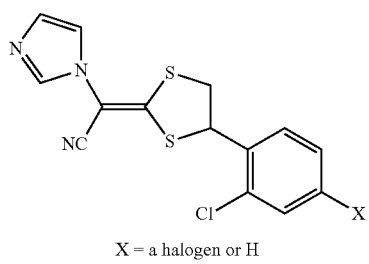

General formula (1)

X = a halogen or H

It is generally known that an antifungal agent is used for a therapy for tinea (tinea pedis, tinea corporis, or tinea cruris), candidiasis (intertrigo or erosio interdigitalis blastomycetica), chromophytosis, or seborrheic dermatitis, for example. However, a formulation used for seborrheic dermatitis is applied to a scalp site around the hair, and thus is used in a larger amount compared with that used for mycoses of the body and mycoses of the hands and feet. Therefore, it is restricted to use a solvent such as methyl ethyl ketone from the viewpoints of possibility of causing an irritation, flammability, and the like. Accordingly, there has been a demand for a formulation that is free of any adverse effect such as an irritation and may be easily administered. In addition, in order to ensure an effect of an antifungal action, it is preferred that a formulation sufficiently dissolves a drug and be in a form of a single-phase solution. Because the compound represented by the general formula (1) has restricted water solubility, one problem is how to prepare a formulation in a form of a single-phase solution without impairing the solubility of the compound.

Meanwhile, various studies are being conducted in order to improve the stability of a bulk drug of an antifungal agent. In particular, in a compound having an asymmetric carbon in the molecule, the maintenance of a steric structure becomes a critical issue in addition to the solubility. This is because the steric structure may be easily changed in a dissolution state. Any of the addition of sugars (see JP 2000-169372 A) and the adjustment of a pH (see JP 06-065076 A) has been conducted as one measure for the above, for example. In addition, it is known that an imidazole derivative is easily dissolved by polyethylene glycol, to thereby provide satisfactory stability (see JP05-070351A). However, there is no definite law for maintenance property of such steric structure. Thus, it may be said that the case where the steric structure may be maintained is rare in itself. Further, such combination is incidentally found out under the present situation. In a formulation containing the compound represented by the general formula (1), there has been no finding about whether or not the maintenance of the steric structure of the compound becomes a problem, and further, it is not known how to achieve such maintenance of the steric structure. Under such backgrounds, in pharmaceutical administration and regulations, there is a demand for means for ensuring the stability suited for the compound represented by the general formula (1).

In addition, an alcohol typified by ethanol and water are widely used medium ingredients in formulation. It is known that those ingredients may cause hydrolysis or the like to affect the stability of an active ingredient. However, there has been no finding that the ingredients have a preferred contribution to the stability in a specified mixing ratio. Further, an anionic surfactant such as sodium dodecyl sulfate has been known to have a surfactant action and an action of promoting medicament permeability, but is not in any way known for its contribution to the stability.

DISCLOSURE OF THE INVENTION

Problem to be solved by the Invention

The present invention has been made under such circumstances. An object of the present invention is to provide a stable formulation having characteristics including containing a compound represented by the general formula (1).

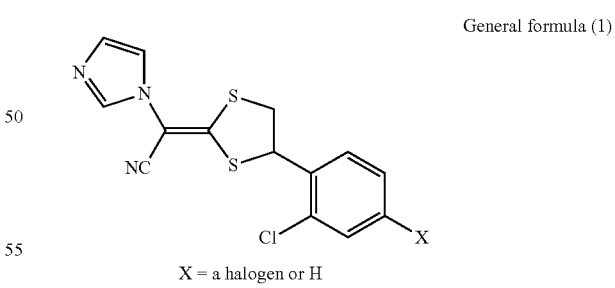

General formula (1)

X = a halogen or H

Means for Solving the Problem

The inventors of the present invention have intensively studied to search a stable formulation having characteristics including containing a compound represented by the general formula (1). As a result, the inventors have found that, in a formulation of a compound represented by the general formula (1), one problem is the maintenance property of a steric structure, and the stability relating to such maintenance property of a steric structure is improved by dissolving the compound in an alcohol and adding a specified proportion of water. The mass ratio of an alcohol to water as described above is 0.1 to 35 mass % of the water with respect to a range of 50 to 95 mass % of the alcohol. It should be noted that such formulation system preferably takes a form of a single-phase solution.

Based on such finding, the inventors of the present invention have completed the present invention. That is, the present invention is as follows.

(1) An antifungal agent for external use, including: 1) a compound represented by the general formula (1); 2) 50 to 95 mass % of an alcohol; and 3) 0.11 to 35 mass % of water and/or an anionic surfactant.

General formula (1)

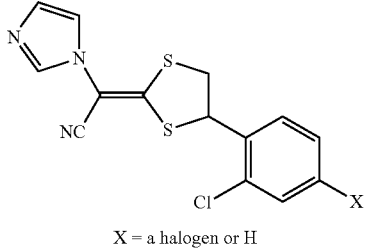

X = a halogen or H (2) The antifungal agent for external use according to the item (1), in which the compound represented by the general formula (1) is luliconazole.

(3) The antifungal agent for external use according to the item (1) or (2), in which the antifungal agent is in a form of a single-phase solution.

(4) The antifungal agent for external use according to any one of the items (1) to (3), including substantially no flammable solvent excluding an alcohol.

(5) The antifungal agent for external use according to any one of the items (1) to (4), wherein a disease to which the antifungal agent is applied is selected from the group consisting of tinea (tinea pedis, tinea corporis, or tinea cruris), candidiasis (intertrigo or erosio interdigitalis blastomycetica), chromophytosis, and seborrheic dermatitis.

(6) The antifungal agent for external use according to the item (5), wherein the disease to which the antifungal agent is applied is seborrheic dermatitis.

Effects of the Invention

The present invention may provide a formulation in which the compound represented by the general formula (1) stably exists. Such formulation may be usefully used for seborrheic dermatitis.

General formula (1)

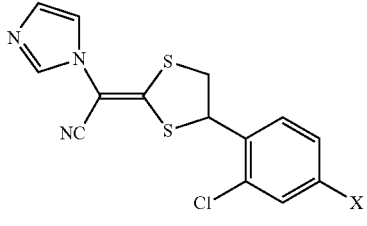

X = a halogen or H

BEST MODE FOR CARRYING OUT THE INVENTION

An antifungal agent for external use of the present invention includes a compound represented by the general formula (1), 50 to 95 mass % of an alcohol such as ethanol, and 0.1 to 35 mass % of water. It should be noted that part or all of water may be replaced by an anionic surfactant.

When X in the compound represented by the general formula (1) represents a halogen, preferred examples of the halogen include a chlorine atom, a bromine atom, an iodine atom, and a fluorine atom. Of those, a chlorine atom is particularly preferred.

Further, the amount of the compound represented by the general formula (1) is preferably 0.01 to 20 mass % and particularly preferably 0.1 to 10 mass % with respect to the total amount of an antifungal agent for external use.

An alcohol typified by ethanol dissolves the compound, and hence is incorporated in an amount of preferably 50 to 95 mass % and further, more preferably 70 to 90 mass % with respect to the total weight of an antifungal agent for external use. This is because the compound may not be sufficiently dissolved and may be time-dependently precipitated when an alcohol amount is small. Therefore, the above-mentioned amount is particularly preferred in order to exhibit a form of a single-phase solution.

Further, alcohols which may be mixed with water at an arbitrary ratio are preferred as alcohols other than ethanol, and specific suitable examples include polyvalent alcohols such as 2-propanol, 2-ethyl-1,3-hexanediol, propylene glycol, 1,3-butanediol, glycerin, and polypropylene glycol. When using those alcohols other than ethanol, they are preferably used together with ethanol, and a form in which ethanol is used together so that ethanol is incorporated in a amount of 50 mass % or more of an alcohol amount is particularly preferred. It may be said that those alcohols other than ethanol are preferably used in such a form that a part, in particular, a part not more than a half amount of ethanol is replaced by one kind or two or more kinds selected from the alcohols. It should be noted that the term "single-phase solution" as used herein refers to liquid substances dissolved with each other in which no white turbidity is observed and neither liquid crystal nor fine crystal is observed under a polarized light.

In contrast, an excess alcohol amount may impair the degree of freedom in prescription. Further, the addition of water may suppress a time-dependent change of the compound in a formulation, for example, a change of the compound into a compound having a changed steric structure such as an S-E isomer represented by the general formula (2) and a Z isomer represented by the general formula (3), in particular, a change of the compound into the S-E isomer. In order to obtain the effect, the percentage of water is preferably 0.1 to 35 mass % and more preferably 1 to 30 mass % with respect to the total weight of the antifungal agent for external use. In the case of using the formulation as a gel formulation by incorporating other aqueous thickeners and the like, the percentage of water is, for example, preferably 5 to 35 mass % and more preferably 10 to mass % with respect to the total weight of the antifungal agent for external use.

For ingredients for improving the stability of the steric structure of the compound represented by the general formula (1) as described above, there are given anionic surfactants such as sodium dodecyl sulfate and sodium polyoxyethylene (4) lauryl ether phosphate in addition to water, and such ingredients may also be used in place of water. However, in the invention of the present application, it is preferred to use only water without using such ingredients because such ingredients may express an irritation in portions other than the nail. Further, an emulsifying system may be adopted in the skin agent for external use of the present invention. However, in order to take advantage of good skin permeability due to the use of an alcohol such as ethanol as a solvent, it is preferred that the skin agent for external use of the present invention be in a form of a single-phase solution.

In the antifungal external agent according to the invention of the present application, the amount ratio of water to the alcohol is preferably 1:99 to 4:6, more preferably 5:95 to 3:7, and particularly preferably 1:7 to 3:5 at a mass ratio. Further, when an anionic surfactant is incorporated into the antifungal agent for external use according to the invention of the present application, the preferred amount ratio of the anionic surfactant to the alcohol is preferably 1:99 to 4:6. Further, when water and an anionic surfactant are incorporated into the antifungal external agent according to the invention of the present application, the water and the anionic surfactant are incorporated so that the ratio of the water to the anionic surfactant comes to preferably 20:1 to 1:1.

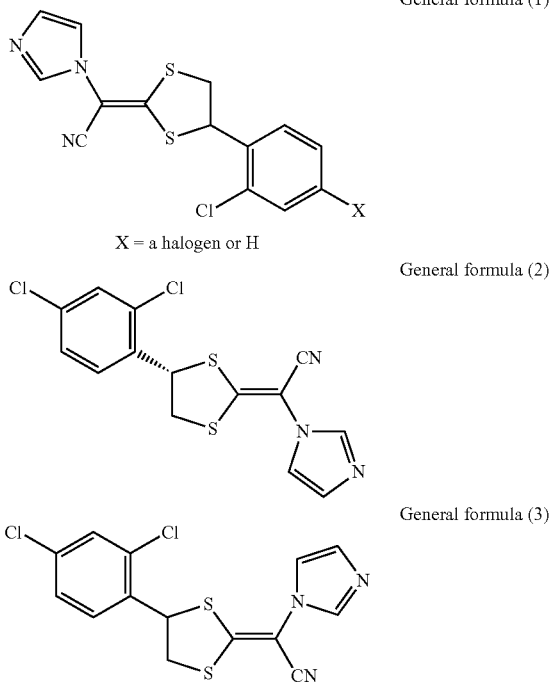

General formula (1)

X = a halogen or H

General formula (2)

General formula (3)

The antifungal agent for external use of the present invention may contain, apart from the above ingredients, an arbitrary ingredient generally used for a skin agent for external use. Preferred examples of the arbitrary ingredient include: oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, hydrogenated coconut oil, hydrogenated oil, Japan wax, hydrogenated castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as oleyl alcohol, cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, diisopropyl adipate, diethyl sebacate, diisopropyl sebacate, di-2-ethylhexyl sebacate, cetyl lactate, diisostearyl malate, ethylene glycol di-2-ethylhexanoate, neopentylglycol dicaprate, di-2-heptyl undecanoic acid glyceride, tri-2-ethylhexanoic acid glyceride, trimethylolpropane tri-2-ethylhexanoate, trimethylolpropane triisostearate, and pentane erythrite tetra-2-ethylhexanoate; oil solutions of silicone oil which is not classified into the above-mentioned silicones and the like such as modified polysiloxanes including amino-modified polysiloxane, polyether-modified polysiloxane, alkyl-modified polysiloxane, and fluorine-modified polysiloxane; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazolinium-hydroxide-1-carboxyethyloxy-2-sodium salt), betaine-based surfactants (such as alkyl betaine, amide betaine, and sulfo betaine), and acylmethyl taurine; nonionic surfactants such as sorbitan fatty acid esters (such as sorbitan monostearate, sorbitan monolaurate, and sorbitan sesquioleate), glycerin fatty acids (such as glycerin monostearate), propyleneglycol fatty acid esters (such as propyleneglycol monostearate), hydrogenated castor oil derivatives, glycerol alkyl ethers, POE sorbitan fatty acid esters (such as POE sorbitan monooleate, polyoxyethylene sorbitan monostearate, and polyoxyethylene sorbitan monolaurate), POE sorbitol fatty acid esters (such as POE-sorbitol monolaurate), POE glycerol fatty acid esters (such as POE-glycerylmonoisostearate), POE fatty acid esters (such as polyethyleneglycol monooleate and POE distearate), POE alkyl ethers (such as POE lauryl ether, POE oleyl ether, and POE 2-octyldodecyl ether), POE alkyl phenyl ethers (such as POE octylphenyl ether and POE nonylphenyl ether), pluronic types, POE/POP alkyl ethers (such as POE/POP 2-decyltetradecyl ether), tetronic types, POE castor oil/hydrogenated castor oil derivatives (such as POE castor oil and POE hydrogenated castor oil), sucrose fatty acid esters, and alkyl glycosides; polyvalent alcohols; moisture ingredients such as sodium pyrrolidone carboxylate, lactic acid, and sodium lactate; pH adjusters such as phosphoric acid and citric acid; powders such as mica, talc, kaolin, synthetic mica, and barium sulfate, whose surfaces may be treated; inorganic pigments such as colcothar, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic powders such as a polyethylene powder, polymethyl methacrylate, a nylon powder, and an organopolysiloxane elastomer; a p-aminobenzoate-based ultraviolet absorbent; an anthranilate-based ultraviolet absorbent; a salicylate-based ultraviolet absorbent; a cinnamate-based ultraviolet absorbent; a benzophenone-based ultraviolet absorbent; a sugar-based ultraviolet absorbent; ultraviolet absorbents such as 2-(2'-hydroxy-5'-t-octylphenyl)benzotriazole and 4-methoxy-4'-t-butyldibenzoylmethane; lower alcohols such as ethanol and isopropanol; vitamins such as vitamin A and derivatives thereof, vitamin Bs such as vitamin $B_6$ hydrochloride, vitamin $B_6$ tripalmitate, vitamin $B_6$ dioctanoate, vitamin $B_2$ and derivatives thereof, vitamin $B_{12}$, and vitamin $B_{15}$ and derivatives thereof, vitamin Es such as α-tocopherol, β-tocopherol, γ-tocopherol, and vitamin E acetate, vitamin Ds, vitamin H, pantothenic acid, pantethine, and pyrroloquinoline quinone; and solvents such as benzyl alcohol, triacetin, crotamiton, carbonic diesters such as prolene carbonate, and ethylene glycol salicylate.

When the antifungal agent for external use of the present invention is applied to seborrheic dermatitis, the antifungal agent preferably has an appropriate viscosity for the purpose of preventing a medicament from being dissipated by dripping to sites other than the applied site. To this end, it is preferred to incorporate a cellulose-based thickener such as carboxymethylcellulose, hydroxypropylcellulose, hydroxypropylmethylcellulose, and ethylcellulose, and a gelling agent such as a methyl vinyl ether-maleic anhydride copolymer, an acrylic resin alkanolamine solution, polyvinylpyrrolidone, and a carboxyvinyl polymer which may be modified with an alkyl group. The total amount of such gelling agent is preferably 0.01 to 5 mass % and more preferably 0.1 to 2.5 mass % with respect to the total amount of the antifungal agent for external use. This is because an effect of preventing dripping may not be exerted when the amount is too small, and a form of a single-phase solution as one preferred mode may be impaired when the amount is too large.

Further, in the antifungal agent for external use of the present invention, a flammable solvent such as methyl ethyl ketone and N-methyl-2-pyrrolidone excluding an alcohol typified by ethanol out of solvents may be incorporated. It is preferred to incorporate the flammable solvent in an amount of 1 mass % or less with respect to the total amount of the antifungal agent for external use, and it is more preferred to incorporate substantially no flammable solvent. This is because, even if such solvent does not exist, a form of a single-phase solution may be achieved in the construction of the antifungal agent for external use of the present invention, and negative factors such as possibility of causing an irritation and flammability possessed by the solvent may be eliminated. The term "flammable solvent" as used herein refers to special flammables and first class petroleum designated under the Fire Defense Law.

The antifungal agent for external use of the present invention may be produced by treating the above-mentioned essential ingredient, preferred ingredient, arbitrary ingredient, and the like in accordance with a conventional method, and for example, is preferably produced by such procedure as shown in the following examples. The antifungal agent for external use of the present invention produced as described above is applied to, for example, cosmetics involving quasi drugs, skin pharmaceutical compositions for external use, and skin goods for external use, and is particularly preferably applied to antifungal skin medicines for external use. The antifungal agent for external use is preferably applied to skin medicines for seborrheic dermatitis for external use that are applied to a wide range of sites and are administered to sites sensitive to an irritation because the properties of the antifungal agent may be highly utilized. However, the antifungal agent for external use may also be effectively applied to mycoses of the body such as tinea corporis, mycoses of the hands and feet such as tinea pedis, and onychomycosis such as tinea unguium, and hence, the application of the antifungal agent to such mycoses also falls within the technical scope of the present invention.

Hereinafter, the present invention is described in more detail by way of examples. However, it goes without saying that the present invention is not limited to only such examples.

Example 1

Luliconazole was dissolved by adding an appropriate amount of ethanol. To the resulting solution, POE (20) sorbitan monostearate ("NIKKOL TS-10MV"; manufactured by Nihon Surfactant Kogyo K.K.) was gradually added, water was further added, and homogenization was performed (Table 1). The resultant was named as Skin agent A for external use. Further, Skin agent B for external use as a control was prepared in the same manner as in Skin agent A for external use except that ethanol was added in place of water.

TABLE 1

| Prescription of Skin agent A for external use | |
|---|---|
| Ingredient | mass % |
| Luliconazole | 1.2 |
| POE (20) sorbitan monostearate | 7.5 |
| Water | 23.3 |
| Ethanol | 68 |
| Total | 100 |

Form of formulation: a form of a single-phase and homogeneously dissolved solution was confirmed through a visual check.

No irritating sensation of the formulation was confirmed.

For Skin agent A for external use and Skin agent B for external use, the time-dependent stability of luliconazole was evaluated 1 week after preparation under a preservation condition at 60° C. The quantitative determination of an S-E isomer in which the steric structure of luliconazole was changed was performed by HPLC (LC-20AD manufactured by Shimadzu Corporation, HPLC condition: column; CHIRALCEL OD-RH 4.6×150 mm, column temperature; 35° C., mobile phase; a mixed solution of methanol/1.8% potassium hexafluorophosphate aqueous solution (83:17, v/v), flow rate; 0.56 mL/min., and detection; 295 nm). Further, the quantitative determination of a Z isomer and other analogous substances was performed by HPLC (Agilent 1100 manufactured by Agilent Technologies, HPLC condition: column; Inertsil ODS-2 4.6×150 mm, column temperature; 40° C., mobile phase; a 0.13% sodium 1-undecane-sulfonate mixed (water/acetonitrile/acetic acid (100) (54:45:1, v/v/v)) solution, flow rate; 1.0 mL/min., and detection; 295 nm). Table 2 shows the results.

TABLE 2

| | Skin agent A for external use | | | Skin agent B for external use | | |
|---|---|---|---|---|---|---|
| Preservation period | S-E isomer (%) | Z isomer (%) | Other analogous substances (%) | S-E isomer (%) | Z isomer (%) | Other analogous substances (%) |
| At time of start | 0.13 | 0.00 | 0.00 | 0.15 | 0.00 | 0.00 |
| 1 week | 0.88 | 0.07 | 0.05 | 4.48 | 0.18 | 0.31 |

Example 2

In the same manner as in Example 1, luliconazole was dissolved in ethanol. To the resulting solution, POE (20) sorbitan monooleate ("NIKKOL TO-10MV"; manufactured by Nihon Surfactant Kogyo K.K.) was gradually added, water was further added, and homogenization was performed to prepare Skin agent C for external use. Further, Skin agent D for external use as a control was prepared in the same manner as in Skin agent C for external use except that ethanol was added in place of water.

TABLE 3

Prescription of Skin agent C for external use

| Ingredient | mass % |
|---|---|
| Luliconazole | 1.2 |
| POE (20) sorbitan monooleate | 9.3 |
| Water | 23.3 |
| Ethanol | 66.2 |
| Total | 100 |

Form of formulation: a form of a single-phase and homogeneously dissolved solution was confirmed through a visual check.
No irritating sensation of the formulation was confirmed.

For Skin agent C for external use and Skin agent D for external use, the time-dependent stability of luliconazole was evaluated 1 week after preparation under a preservation condition at 60° C. The quantitative determination of analogous substances was performed by HPLC under the same analysis condition as that in Example 1. Table 4 shows measurement results.

TABLE 4

| | Skin agent C for external use | | | Skin agent D for external use | | |
|---|---|---|---|---|---|---|
| Preservation period | S-E isomer (%) | Z isomer (%) | Other analogous substances (%) | S-E isomer (%) | Z isomer (%) | Other analogous substances (%) |
| At time of start | 0.14 | 0.00 | 0.00 | 0.13 | 0.00 | 0.00 |
| 1 week | 0.46 | 0.05 | 0.05 | 2.69 | 0.11 | 0.31 |

Example 3

In the same manner as in Example 1, luliconazole was dissolved in ethanol. To the resulting solution, polyoxyethylene hydrogenated castor oil 40 ("NIKKOL HCO-40"; manufactured by Nihon Surfactant Kogyo K.K.) was gradually added, water was further added, and homogenization was performed to prepare Skin agent E for external use. Further, Skin agent F for external use as a control was prepared in the same manner as in Skin agent E for external use except that ethanol was added in place of water.

TABLE 5

Prescription of Skin agent E for external use

| Ingredient | mass % |
|---|---|
| Luliconazole | 1.2 |
| Polyoxyethylene hydrogenated castor oil 40 | 1.4 |
| Water | 23.7 |
| Ethanol | 73.7 |
| Total | 100 |

Form of formulation: a form of a single-phase and homogeneously dissolved solution was confirmed through a visual check.
No irritating sensation of the formulation was confirmed.

For Skin agent E for external use and Skin agent F for external use, the time-dependent stability of luliconazole was evaluated 1 week after preparation under a preservation condition at 60° C. The quantitative determination of analogous substances was performed by HPLC under the same analysis condition as that in Example 1. Table 6 shows measurement results.

TABLE 6

| | Skin agent E for external use | | | Skin agent F for external use | | |
|---|---|---|---|---|---|---|
| Preservation period | S-E isomer (%) | Z isomer (%) | Other analogous substances (%) | S-E isomer (%) | Z isomer (%) | Other analogous substances (%) |
| At time of start | 0.13 | 0.00 | 0.00 | 0.13 | 0.00 | 0.00 |
| 1 week | 0.28 | 0.04 | 0.04 | 0.57 | 0.05 | 0.00 |

Example 4

In the same manner as in Example 1, luliconazole was dissolved in ethanol. To the resulting solution, polyethylene glycol 200 ("PEG-200"; manufactured by TOHO Chemical Industry Co., LTD.) was gradually added, water was further added, and homogenization was performed to prepare Skin agent G for external use. Further, Skin agent H for external use as a control was prepared in the same manner as in Skin agent G for external use except that ethanol was added in place of water.

TABLE 7

Prescription of Skin agent G for external use

| Ingredient | mass % |
|---|---|
| Luliconazole | 1.2 |
| Polyethylene glycol 200 | 18.5 |
| Water | 17.3 |
| Ethanol | 63 |
| Total | 100 |

Form of formulation: a form of a single-phase and homogeneously dissolved solution was confirmed through a visual check.
No irritating sensation of the formulation was confirmed.

For Skin agent G for external use and Skin agent H for external use, the time-dependent stability of luliconazole was evaluated 1 week after preparation under a preservation condition at 60° C. The quantitative determination of analogous substances was performed by HPLC under the same analysis condition as that in Example 1. Table 8 shows measurement results.

TABLE 8

| | Skin agent G for external use | | | Skin agent H for external use | | |
|---|---|---|---|---|---|---|
| Preservation period | S-E isomer (%) | Z isomer (%) | Other analogous substances (%) | S-E isomer (%) | Z isomer (%) | Other analogous substances (%) |
| At time of start | 0.13 | 0.00 | 0.00 | 0.14 | 0.00 | 0.00 |
| 1 week | 0.22 | 0.04 | 0.00 | 0.69 | 0.04 | 0.00 |

Example 5

In the same manner as in Example 1, luliconazole was dissolved in ethanol. To the resulting solution, hydroxypropylmethylcellulose 2910 ("METOLOSE 60SH-4000"; manufactured by Shin-Etsu Chemical Co., Ltd.) was gradually added and homogeneously dispersed. Then, water was added to prepare skin agents for external use. The skin agents for external use having water amounts of 23.6 mass % and 17.9 mass % with respect to the total mass were named as Skin agent I for external use and Skin agent J for external use, respectively. Further, Skin agent K for external use as a control was prepared in the same manner as in Skin agent J for external use except that ethanol was added in place of water.

TABLE 9

| Prescription of Skin agent I for external use | |
|---|---|
| Ingredient | mass % |
| Luliconazole | 1.2 |
| Hydroxypropylmethylcellulose 2910 | 1.2 |
| Water | 23.6 |
| Ethanol | 74 |
| Total | 100 |

Form of formulation: a form of a single-phase and homogeneously dissolved solution was confirmed through a visual check.
No irritating sensation of the formulation was confirmed.

For Skin agent I for external use, Skin agent J for external use, and Skin agent K for external use, the time-dependent stability of luliconazole was evaluated 1 week after preparation under a preservation condition at 60° C. The quantitative determination of analogous substances was performed by HPLC under the same analysis condition as that in Example 1. Table 10 shows measurement results.

TABLE 10

| | Skin agent I for external use | | | Skin agent J for external use | | | Skin agent K for external use | | |
|---|---|---|---|---|---|---|---|---|---|
| Preservation period | S-E isomer (%) | Z isomer (%) | Other analogous substances (%) | S-E isomer (%) | Z isomer (%) | Other analogous substances (%) | S-E isomer (%) | Z isomer (%) | Other analogous substances (%) |
| At time of start | 0.14 | 0.00 | 0.00 | 0.15 | 0.02 | 0.00 | 0.18 | 0.00 | 0.00 |
| 1 week | 2.83 | 0.12 | 0.07 | 3.78 | 0.16 | 0.03 | 9.08 | 0.44 | 0.22 |

Example 6

In the same manner as in Example 1, luliconazole was dissolved in ethanol. To the resulting solution, sodium dodecyl sulfate ("NIKKOL SLS"; manufactured by Nikko Chemicals Co., Ltd.) was gradually added and homogeneously dispersed to prepare Skin agent L for external use. Further, Skin agent M for external use as a control was prepared in the same manner as in Skin agent L for external use except that ethanol was added in place of sodium dodecyl sulfate.

TABLE 11

| Prescription of Skin agent L for external use | |
|---|---|
| Ingredient | mass % |
| Luliconazole | 1.2 |
| Sodium dodecyl sulfate | 2 |
| Ethanol | 96.8 |
| Total | 100 |

For Skin agent L for external use and Skin agent M for external use, the time-dependent stability of luliconazole was evaluated 1 week after preparation under a preservation condition at 60° C. The quantitative determination of analogous substances was performed by HPLC under the same analysis condition as that in Example 1. Table 12 shows measurement results.

TABLE 12

| | Skin agent L for external use | | | Skin agent M for external use | | |
|---|---|---|---|---|---|---|
| Preservation period | S-E isomer (%) | Z isomer (%) | Other analogous substances (%) | S-E isomer (%) | Z isomer (%) | Other analogous substances (%) |
| At time of start | 0.13 | 0.00 | 0.00 | 0.17 | 0.02 | 0.00 |
| 1 week | 0.66 | 0.05 | 0.00 | 1.45 | 0.09 | 0.00 |

Those results have revealed that a single-phase solution or a gel formulation may be prepared by dissolving luliconazole with an alcohol typified by ethanol in the skin agent for external use, and adding water and the like, and an increase in the S-E isomer and the Z isomer having different steric structures of luliconazole may be suppressed compared with the case where water and the like are not compounded.

Example 7

Skin agent for external use N was prepared in the same operation as that in Example 6 in accordance with the following prescription. After preservation at 60° C. for 1 week, the amount of the S-E isomer was measured by the above-mentioned technique, and as a result, a peak of the S-E isomer was detected only at a trace level. The skin agent for external use N is found out to have a similar effect.

TABLE 13

| Ingredient | mass % |
|---|---|
| Ethanol | 35.4 |
| Water | 17.4 |
| 2-propanol | 46 |
| Luliconazole | 1.2 |
| Total | 100 |

Example 8

Skin agent for external use O was prepared in the same operation as that in Example 7 in accordance with the following prescription. After preservation at 60° C. for 1 week, the amount of the S-E isomer was measured by the above-mentioned technique, and as a result, a peak of the S-E isomer was detected only at a trace level. The skin agent for external use O is found to have a similar effect.

TABLE 14

| Ingredient | mass % |
|---|---|
| Ethanol | 64.6 |
| Water | 23.3 |
| 2-ethyl-1,3-hexanediol | 10.9 |
| Luliconazole | 1.2 |
| Total | 100 |

Skin agent for external use P was prepared in the same operation as that in Example 8 in accordance with the following prescription. After preservation at 60° C. for 1 week, the mass of the other analogous substances was measured by the above-mentioned technique, and as a result, peaks corresponding to the substances were not observed. The skin agent for external use P is found to have a similar effect.

TABLE 15

| Ingredient | mass % |
|---|---|
| Ethanol | 69.7 |
| Water | 5.8 |
| Polypropylene glycol 2000 | 23.3 |
| Luliconazole | 1.2 |
| Total | 100 |

INDUSTRIAL APPLICABILITY

The preparation may be performed by compounding an alcohol such as ethanol and water in certain ranges into the compound represented by the general formula (1), to thereby improve the stability of the compound in a formulation.

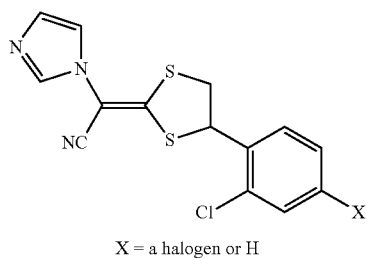

General formula (1)

X = a halogen or H

What is claimed is:

1. An antifungal composition for external use, consisting essentially of: 1) luliconazole; 2) 50 to 95 mass % of an alcohol; and 3) 0.1 to 35 mass % of a third component selected from the group consisting of water, an amount of an anionic surfactant, and the combination of water and anionic surfactant whereby isomerization of the steric structure of the luliconazole is suppressed.

2. The antifungal composition for external use according to claim 1, wherein the composition is in a form of a single-phase solution.

3. The antifungal composition for external use according to claim 1, comprising substantially no flammable solvent excluding an alcohol.

4. The antifungal composition for external use according to claim 1, wherein formation of Z isomer is suppressed in the composition.

5. The antifungal composition according to claim 1 further comprising one or more selected from the group consisting of oils or waxes, higher fatty acids, synthetic ester oils, oil solutions of silicone oil, silicones, cationic surfactants, amphoteric surfactants, nonionic surfactants, moisture ingredients, pH adjusters, powders, inorganic pigments, pearl agents, organic dyes, organic powders, vitamins, UV absorbents, thickeners and gelling agents.

6. The antifungal composition according to claim 1 further comprising one or more selected from the group consisting of liquid paraffin, squalane, pristane, ozokerite, paraffin, ceresin, vaseline, and microcrystalline wax.

7. The antifungal composition according to claim 1, wherein the alcohol is present in an amount of 63-74 mass %.

8. The antifungal composition according to claim 1 wherein the water is present in an amount of 5.8-23.7 mass %.

9. The antifungal composition according to claim 1, wherein the anionic surfactant is present in an amount of 0.5-63 mass %.

10. The antifungal composition according to claim 1, which contains no surfactant.

11. A method for treating mycosis comprising administering transdermally to a subject in need thereof a composition consisting essentially of: 1) luliconazole; 2) 50 to 95 mass % of an alcohol; and 3) 0.1 to 35 mass % of a third component selected from the group consisting of water, an amount of an anionic surfactant and the combination of water and anionic surfactant, whereby isomerization of the steric structure of the luliconazole is suppressed,

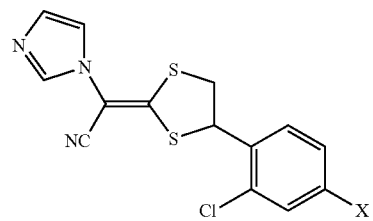

12. The method according to claim 11, wherein the composition is in a form of a single-phase solution.

13. The method according to claim 11, wherein the composition comprises substantially no flammable solvent excluding an alcohol.

14. The method according to claim 11, wherein the mycosis is selected from the group consisting of tinea, candidiasis, chromophytosis, and seborrheic dermatitis.

15. The method according to claim 14, wherein the mycosis is seborrheic dermatitis.

16. A method for stabilizing luliconazole in medicine consisting essentially of adding 1) 50 to 95 mass % of an alcohol; and 2) 0.1 to 35 mass % of a component selected from the group consisting of water, an amount of an anionic surfactant and the combination of water and anionic surfactant, to a pharmaceutical composition, whereby isomerization of the steric structure of the luliconazole is suppressed.

17. The method according to claim 16, wherein the stabilizing effects are depletion of production of their isomers.

18. The method according to claim 17, wherein the isomer(s) are E form and/or Z form of luliconazole.

* * * * *

UNITED STATES PATENT AND TRADEMARK OFFICE
CERTIFICATE OF CORRECTION

PATENT NO. : 8,513,296 B2
APPLICATION NO. : 13/603220
DATED : August 20, 2013
INVENTOR(S) : Takaaki Masuda et al.

It is certified that error appears in the above-identified patent and that said Letters Patent is hereby corrected as shown below:

On the Title Page
At Page 2 (Item 56), Column 2, Lines 18-19, under Other Publications, below "2004." please delete "Article, "Treatment" in 2 pages downloaded from http://www.babymd.net/dryskin.htm date unknown.".

In the Specification
At Column 3, Line 13, please change "0.11" to --0.1--.
At Column 4, Line 52, after "to" please insert --30--.

In the Claims
At Column 13, Line 59, in Claim 1, after "of" please delete "the steric structure of the".
At Column 14, Lines 2-3, in Claim 4, please change "suppressed in the composition." to --suppressed.--.
At Column 14, Lines 31-32, in Claim 11, after "of" please delete "the steric structure of the".
At Column 14, Line 32, in Claim 11, please change "suppressed," to --suppressed.--.
At Column 14, Lines 35-40, in Claim 11, below "suppressed," please delete "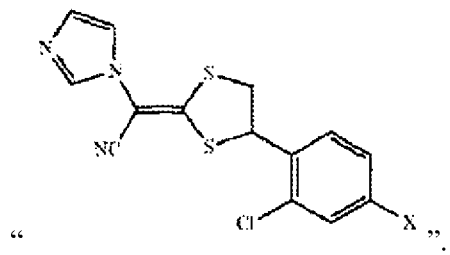".

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,513,296 B2

At Column 14, Lines 59-60, in Claim 16, after "of" please delete "the steric structure of the".

At Column 14, Line 62, in Claim 17, please change "depletion of production of their isomers." to --inhibition of isomerization.--.